United States Patent
Akerfeldt et al.

(10) Patent No.: US 6,196,980 B1
(45) Date of Patent: *Mar. 6, 2001

(54) MALE CONNECTOR WITH A CONTINUOUS SURFACE FOR A GUIDE WIRE, AND METHOD THEREFOR

(75) Inventors: Dan Akerfeldt; Peter Jensen, both of Uppsala; Ola Hammarstroem, Alunda, all of (SE)

(73) Assignee: Radi Medical System AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/333,031

(22) Filed: Jun. 15, 1999

Related U.S. Application Data

(63) Continuation-in-part of application No. 08/927,677, filed on Sep. 10, 1997, now Pat. No. 5,938,624.

(51) Int. Cl.[7] ........................................ A61B 5/00
(52) U.S. Cl. ............................................... 600/585
(58) Field of Search .................... 600/506, 585; 607/116, 122, 124

(56) References Cited

U.S. PATENT DOCUMENTS

| | | | |
|---|---|---|---|
| 2,238,834 | 4/1941 | Travers | 173/361 |
| 3,289,149 | 11/1966 | Pawloski | 339/183 |
| 3,766,512 | 10/1973 | Falbet | 339/14 R |
| 4,603,696 | 8/1986 | Cross, Jr. et al. | 128/419 P |
| 4,711,027 | 12/1987 | Harris | 29/869 |
| 4,850,359 | 7/1989 | Putz | 128/642 |
| 4,958,642 | 9/1990 | Christian et al. | 128/772 |
| 4,961,433 | 10/1990 | Christian | 128/772 |
| 4,967,753 | 11/1990 | Haase et al. | 128/662.06 |
| 5,105,818 | 4/1992 | Christian et al. | 128/662.06 |
| 5,141,444 | 8/1992 | Redmond et al. | 439/59 |
| 5,178,159 | 1/1993 | Christian | 128/772 |
| 5,240,437 | 8/1993 | Christian | 433/668 |
| 5,357,979 | 10/1994 | Imran | 600/585 |
| 5,509,411 | 4/1996 | Littman et al. | 128/642 |

Primary Examiner—Max Hindenburg
(74) Attorney, Agent, or Firm—Foley & Lardner

(57) ABSTRACT

A male connector with a continuous surface is provided for a guide wire. The male connector includes a core wire (1), and conductive members (5) spaced apart longitudinally along the core wire (1). An insulating material (9) is disposed between the core wire (1) and the conductive members (5), the insulating material having an outer surface coextensive with outer surfaces of the conductive members (5). Conductors (7), disposed along the core wire (1), are connected to the conductive members (5). The outer surface of the insulating material and the outer surfaces of the conductive members (5) are substantially smooth.

22 Claims, 10 Drawing Sheets

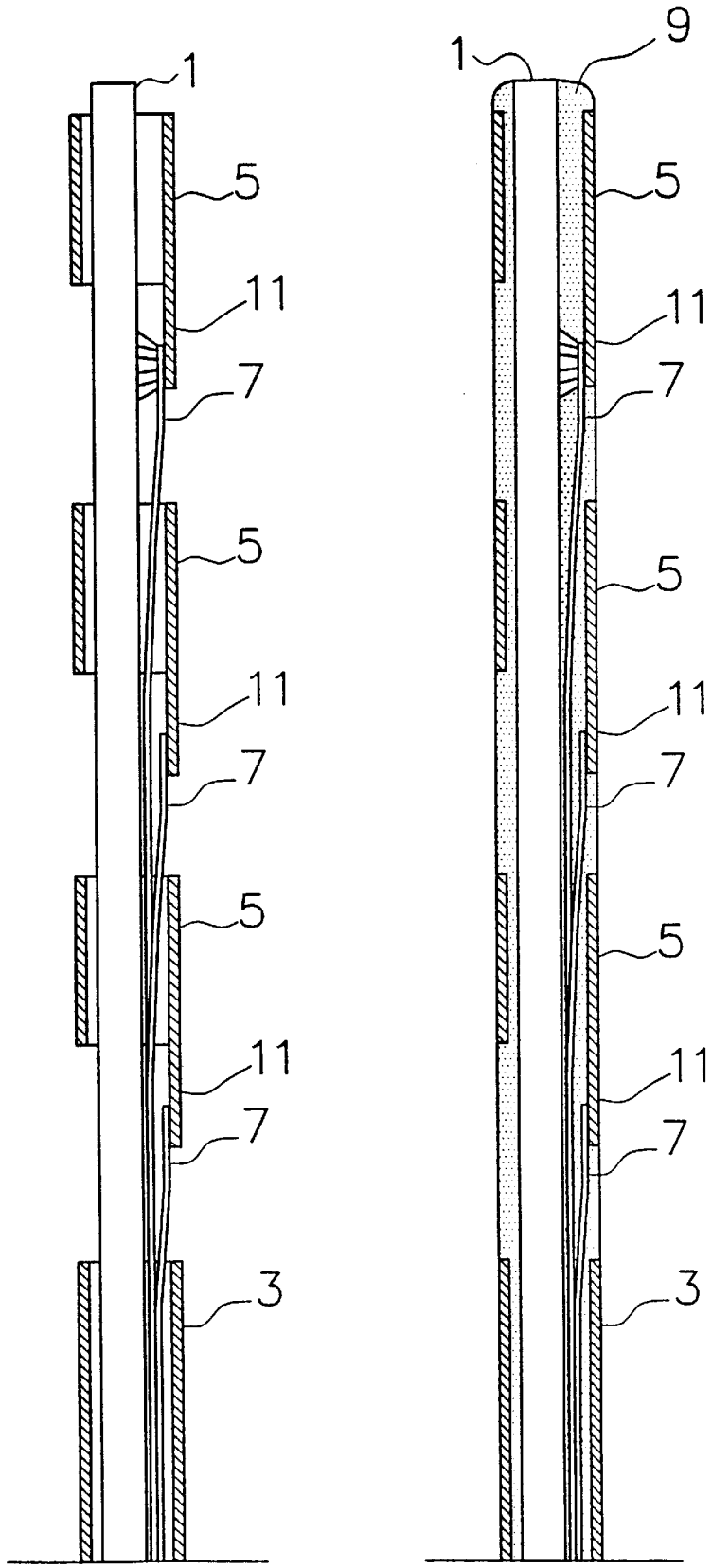

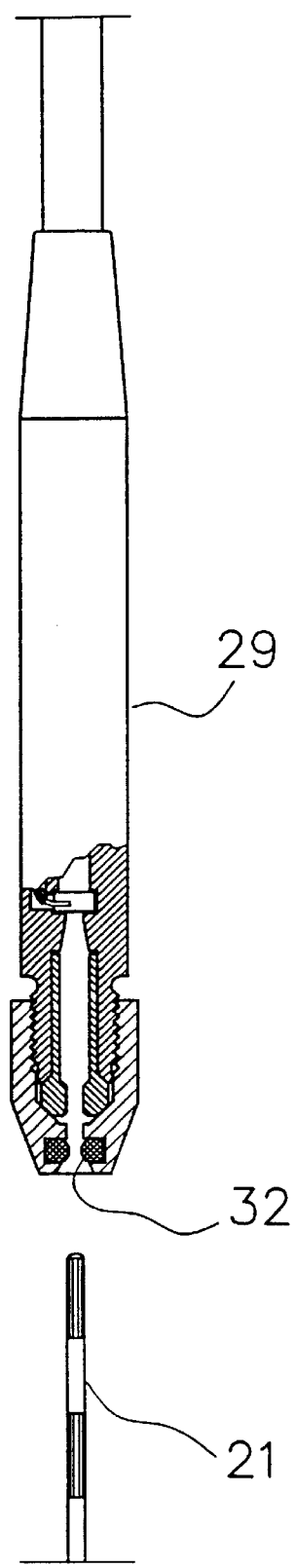
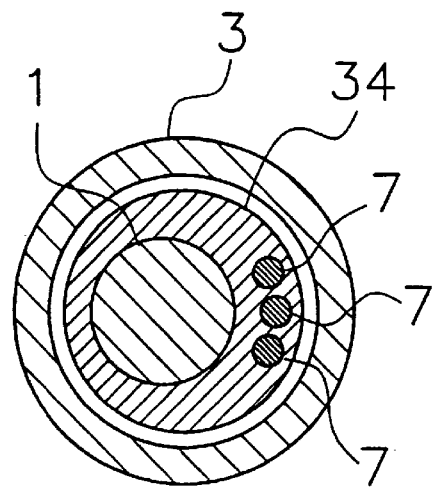
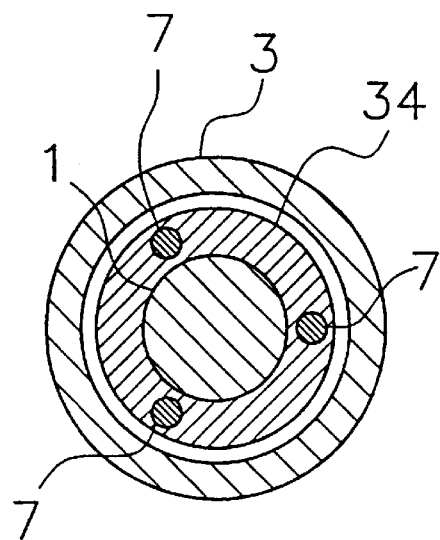
FIG.14
FIG.13
FIG.12

MALE CONNECTOR WITH A CONTINUOUS SURFACE FOR A GUIDE WIRE, AND METHOD THEREFOR

The applicants hereby claim the benefit of prior U.S. patent application Ser. No. 08/927,677, filed Sep. 10, 1997 now U.S. Pat. No. 5,938,624 and entitled "Male Connector with a Continuous Surface for a Guide Wire and Method Therefor". The entire contents of this Ser. No. 08/927,677 application is incorporated herein by reference. Also, the entire contents of Patent Cooperation Treaty (PCT) Publication WO 99/13532, published Mar. 18, 1999, is incorporated herein by reference.

BACKGROUND OF THE INVENTION

The invention concerns a male connector for a guide wire. More specifically, the invention concerns a male connector with conductors, presenting a continuous outer surface to preclude contamination of conductors.

Guide wires are generally known in the art. Their use is, for example, in connection with the treatment of coronary disease. As is conventional, a contrast media is used in connection with an x-ray of a blood vessel to show occlusion, however, without showing a cross section of a stenosis. Complicating the diagnosis of the problem is that different patients have different blood flow. It is accepted that measurement of the pressure is the best way to diagnose the significance of the stenosis. In use of the guide wire, it is introduced into the femoral artery and then positioned in the desired area. Once the guide wire is positioned, a catheter is introduced over the guide wire. A balloon dilation may then be done. An electrical connector is desirable to use at the proximal end of the guide wire, permitting a change of the catheter. However, such changeable connectors may be contaminated by blood and other bodily fluids at the time the catheter is changed.

A guide wire assembly with connectors is shown, for example, in U.S. Pat. No. 5,178,159, Christian. These connectors, however, do not work well after blood contamination, which may cause a short circuit. In addition, the '159 patent is an example of a connector with crevices which are difficult to clean.

Other electrical connectors are known, however, not used within the guide wire situation which requires an extremely small size connector. U.S. Pat. No. 3,289,149, Palowski, shows a multiple contact jack assembly. Such a construction, which however may show what appears to be continuous surface, in fact has joints which create a capillary action allowing penetration of bodily fluids therein. With the small size required by the guide wire, the bodily fluids can create a short circuit in the contact.

Other conventional electric connector plugs and sockets are known. These include, for example, U.S. Pat. No. 2,238,834, Travers; U.S. Pat. No. 3,766,512, Falbet. Again, these are relatively large devices and unusable in connection with a guide wire.

Consequently, there remains a need for a contact which can be used with the restricted small size of a guide wire, which has a cylindrical or smooth outer surface which is easy to clean from blood. In addition, there remains a need for a contact which can be used in situations where there might be contamination by human or animal body fluid, which avoids contamination by those fluids which could otherwise cause a short circuit.

In addition, there is a need for a male connector for a guide wire which can be automatically cleaned upon connection to the female member.

Further need in the industry is for a guide wire male connector which is relatively straightforward to manufacture, in spite of the restricted small size imposed by using as part of a guide wire.

There is also a need for a guide wire which includes a contact which is as forgiving as possible of handling by the physician, including, for example, bending.

Finally, there remains a need for an improved connector for a guide wire for use in changing catheters.

SUMMARY OF THE INVENTION

It is, therefore, an object of the present invention to provide a male contact which has a smooth, continuous outer surface from which blood is readily cleaned before connecting to a female contact. Additionally, it is the object of the present invention to prevent blood contamination which would otherwise cause a short circuit.

It is yet another object of the present invention to create a male contact which is automatically cleaned upon connection to a female member. A further object of the present invention is to create a contact which is as forgiving as possible of manipulation by the user.

It is yet another object of the invention to provide an improved connector for use on a guide wire in connection with catheters.

It is another object of the present invention to provide a relatively easily manufactured connector useful at the small dimensions of a guide wire.

In accordance with one aspect of the invention, there is provided a male connector for a guide wire. The male connector includes a core wire. There are a plurality of conductive members spaced apart longitudinally along the core wire. A continuous insulating material is disposed between the core wire and the respective conductive members, the insulating material having an outer surface coextensive with outer surfaces of the conductive members. There is at least one conductor, disposed along the core wire, connected to the conductive members.

In accordance with one aspect of the invention, the conductive members include a bent tongue; in another aspect, the conductive members include an unbent tongue.

In accordance with another aspect of the invention, there is provided an insulating coating on the core wire, between the core wire and the conductive members. In accordance with a different aspect of the invention there is provided insulating coatings on the insides of the conductive members.

In accordance with another aspect of the invention, a connector for a guide wire includes the male connector. The female includes a wiper device complementary to the male connector.

In accordance with yet another aspect of the invention, there is provided a method of precluding contamination by human or animal body fluid and the like in an electrical connector having a male member and a female member. An elongated guide wire having a proximal end and a distal end is provided, the male member being positioned at the proximal end thereof. A smooth, coextensive surface is formed on the male member, the male member having a electrical conductors thereon and include insulating material therebetween. The distal end of the guide wire is inserted into the body in the presence of body fluid. A catheter is slid over the guide wire and into the body wherein body fluids surround and enter at least a portion of the catheter. The male member is engaged into the female member, the female member having complementary conductors therein. The male and female members are disengaged. The catheter is removed from the body by sliding the catheter over the guide wire wherein body fluids are deposited on the smooth surface of the male member. The body fluids are removed from the smooth surface without leaving body fluid on or between the conductors, thus precluding contamination.

BRIEF DESCRIPTION OF THE DRAWINGS

In the drawings:

FIG. 5 illustrates a second embodiment of the male connector for a guide wire, prior to final assembly;

FIG. 6 illustrates the second embodiment of the male connector for a guide wire, after final molding;

FIG. 12 illustrates a female connector having a wiper device for cleaning of the male connector for a guide wire;

FIG. 13 illustrates a cross section of a fourth embodiment of the male connector, with conductors equally spaced;

FIG. 14 illustrates a cross section of the fourth embodiment with conductors unequally spaced;

DETAILED DESCRIPTION OF THE PREFERRED EMBODIMENTS

Figures 1, 2:
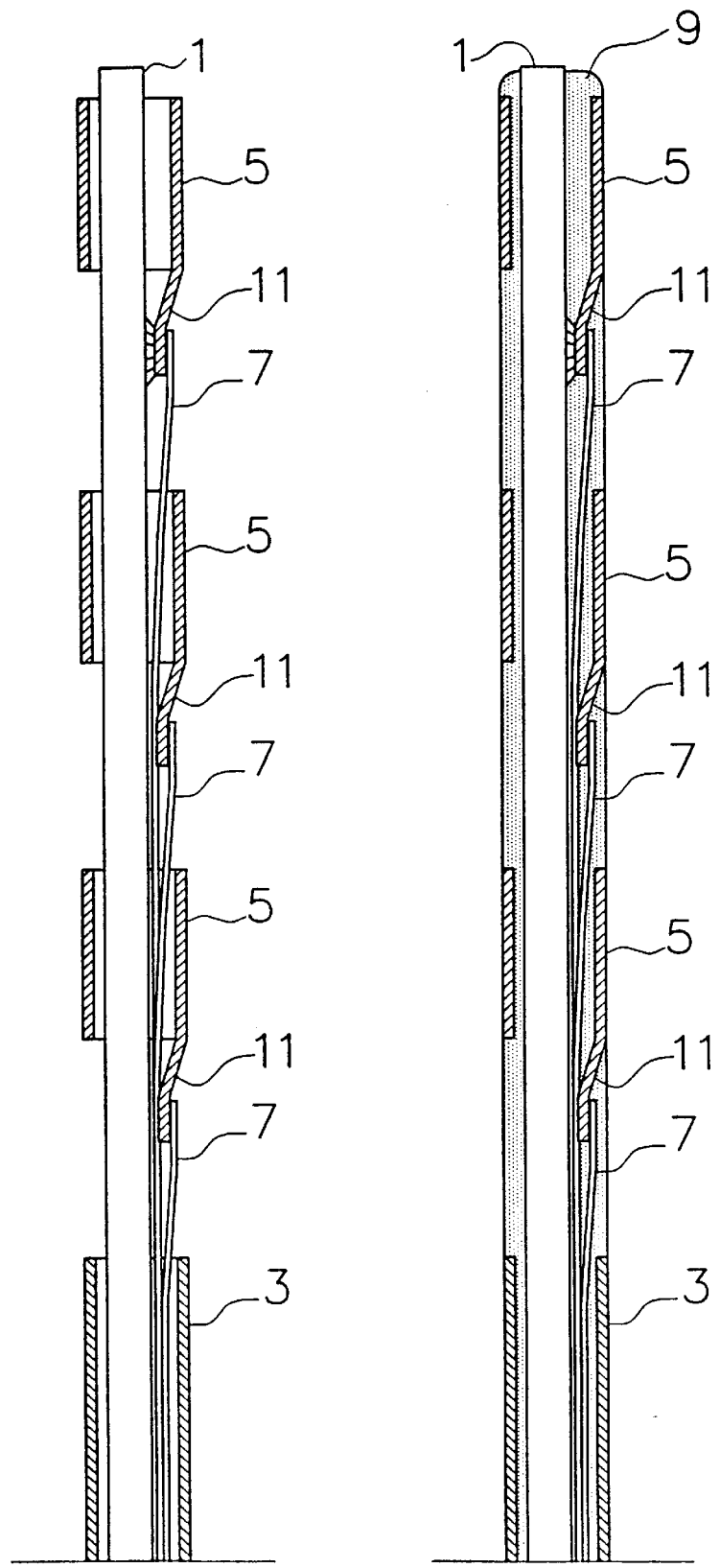
FIG. 1 illustrates the male connector on a guide wire after assembly, and prior to final molding.
FIG. 2 illustrates the male connector for a guide wire after molding.

A male connector for a guide wire is generally illustrated in FIGS. 1 and 2. The male connector is disposed on the proximal end of a guide wire 3. It includes a core wire 1, a plurality of conductive members 5, a plurality of conductors 7, and insulating material 9.

The core wire 1 conventionally extends through a guide wire, and extends from the proximal end. The core wire is conventionally used to prevent kinks, to provide strength to the guide wire, and to hold the guide wire together. Traditionally, it is made of a high strength material, such as, for example, stainless steel. Other high strength materials (including non-metallic materials) can be used. The core wire therefore should be as large a diameter as possible, while leaving room for the conductors and other elements to fit within the catheter within which the guide wire will be used. In the preferred embodiment, the core wire has a diameter of 0.15 millimeter.

The circumference of the entire male connector will be limited by the size of the catheter within which it will be used. Preferably, the guide wire fits snugly within the catheter. The diameter of the entire guide wire which is provided for use within conventional small catheters is 0.355 millimeters. This diameter is, of course, dictated by the size of the conventional catheter. If the catheter size differs, the guide wire and therefore the male connector would be of an equivalent diameter.

The male connector also includes two or more conductive members 5. In the illustrated embodiment, the conductive members are cylindrical. They are spaced apart longitudinally from the other conductive members. The conductive members 5 also are spaced apart from the core wire 1.

Figure 3:
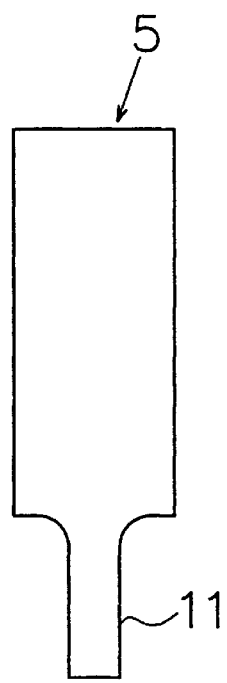
FIG. 3 illustrates one embodiment of a contact member for the male connector f or the guide wire.

FIG. 3 illustrates the conductive member in greater detail. The conductive member preferably includes a tongue 11. In the embodiment illustrated in FIGS. 1–4, the tongue 11 is bent radially inward. The bent shape of the tongue permits the conductor 7 to be positioned on the outside of the tongue, while remaining within the dimensions imposed by the catheter. The conductive members are made from any good conductive material. Preferably, they are machined of platinum. Other possible materials include stainless steel, gold and copper, for example.

Use of a tongue 11 on the conductive member is preferred in order to provide a secure contact to the conductor, within the small size range permitted by the catheter. Specifically, if the conductor is connected directly to the conductive member, there is a danger that conductive material such as solder would extend beyond the outer diameter of the guide wire. Use of a tongue 11 on the conductive member permits placement of a conductor 7 either on the outside of a bent tongue as shown in FIG. 3, or as shown in alternative embodiment of FIGS. 5 and 6, the conductor 7 can be placed on the inside of the tongue.

It will be appreciated that the conductive member 5 is illustrated as being cylindrical. This is a conventional shape, used because of the connection with a corresponding female connector. It will be appreciated that alternative shapes of the conductive member may be permitted, including a pin, or a C-shape, or coiled in the correct form, or even a rectangular strip with, for example, the tongue 11. The conductive member is preferably 4 millimeters in length, excluding the tongue 11. The conductive members (excluding the tongue 11) are generally spaced apart by about 4 millimeters; however, this distance is non-critical.

Each of the conductive members 5 are connected, respectively, to a conductor 7. The conductors 7 are bonded or soldered to the conductive member 5, preferably at the tongue 11.

In the preferred embodiment, the proximal conductive member is additionally connected to the core wire 1 to provide signal ground. As illustrated, the tongue 11 of the proximal conductive member 5 is soldered at position 11 to provide ground. It will be appreciated by those of skill in the art that signal ground can be provided in other ways. The conductors are conventionally of a diameter of 0.04 millimeters.

Illustrated in FIG. 2 is the insulating material 9. As a first step, the male connector shown in FIG. 1 is assembled prior to insertion of the insulating material 9 shown in FIG. 2. As is illustrated in FIG. 2, the insulating material provides the male contact with a smooth outer surface. The smooth outer surface may be easily cleaned from blood for connecting to the female contact. The insulating material is continuous, thereby preventing capillary action from bodily fluid which would otherwise allow a short circuit. Also, the insulating material 9 has an outer surface which is coextensive with an outer surface of the conductive members 5, thereby presenting a relatively smooth surface that can be easily cleaned of blood or bodily fluids with a wiping device, for example, a rubber ring or O-ring mounted in a female contact.

The insulating material 9 is preferably a molded polymer material, which can be injected after the assembly (as previously discussed). The insulating material can be, for example, a two-component epoxy adhesive. The insulating material 9 performs the function in the assembled male connector of spacing apart the core wire 1 from the conductive members 5; it also spaces the respective conductive members 5 apart from each other. In the fully assembled and finished male connector for the guide wire, a relatively smooth, cylindrical outer surface will be presented. In other words, the outer surface of the insulating material 9 is coextensive with outer surfaces of the conductive members 5. The outer diameter of the fully assembled male connector for use with current conventional catheters will be 0.355 millimeters; however, this size accommodates the conventional catheter inside diameter.

It is also possible to provide, as an insulating material, a combination (or composite) of a segment of a thin polymer tubing, positioned between the conductive members 5, for providing the spacing, and insulating material 9. Thereby, the tubing segment provides an outer shell forming a smooth outer surface. This will be further described below with reference to FIGS. 19 and 20.

Figure 4:
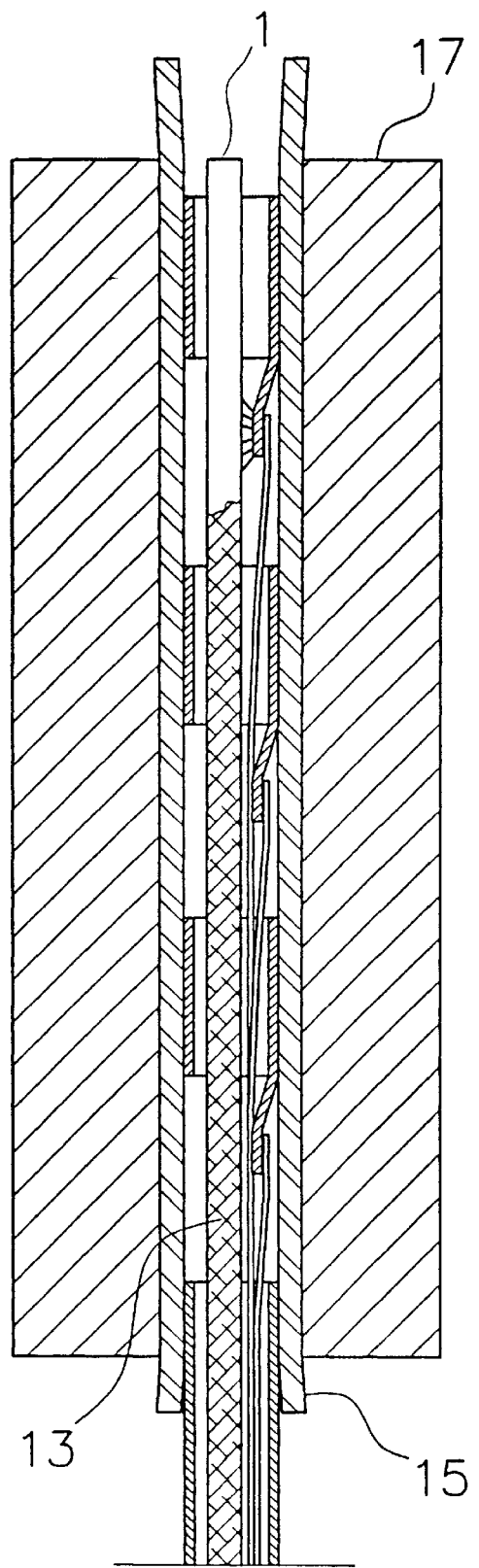
FIG. 4 illustrates the mold tool used in manufacturing the male connector for the guide wire.

FIG. 4 concerns a method for making the male connector for the guide wire. In the preferred method for assembling the male connector, the conductive members 5 are shielded from the core wire by a coating 13. In the embodiment illustrated in FIG. 4, the illustrated coating is on the core wire 1. The coating, for example, an insulating lacquer, prevents a potential short circuit created by contact of the non-grounded conductive members 5 with the core wire 1. Once the insulating material 9 is in place in the finished male connector, there is no further use for the coating 13.

Figure 8:
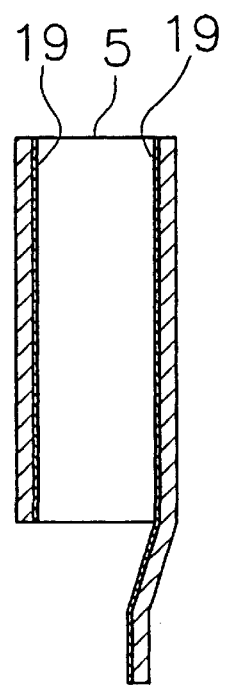
FIG. 8 is a cross-section view of an alternative embodiment of a coating on the conductive member.

In an alternative embodiment, illustrated in FIG. 8, a coating 19 may be provided instead on the inside of the conductive member 5.

After the male connector is partially assembled as shown in FIG. 1, that is, after the conductive members have been connected to the conductors, a flexible tube is threaded onto the male connector. In practice, a plastic tube using polytetrafluoroethylene (PTFE)on the interior is preferred. The tube fits onto the male connector with a slight clearance making it easy to thread. The connector and the tube are then placed into a mold 17, such as a split steel tool. As illustrated, the mold 17 is split into two halves, and as is conventional with molds, the halves can be pressed together. In this embodiment, the plastic tube will be compressed therebetween, so that the conductive members 5 are tightly compressed. The tube 15 is then evacuated, and filled with the insulating material 9 (e.g., two component epoxy) from the proximal end until the male connector is completely filled. After curing, in the preferred embodiment, the tube is removed from the mold. Rolling the tube between two flat metal surfaces permits relatively easy removal of the male connector from the tube.

FIGS. 5 and 6 illustrate an alternative embodiment of the conductive members 5 with tongue 11. As is illustrated here, the tongues 11 are not bent as they were in FIGS. 1 and 2. In FIGS. 5 and 6, the conductors 7 are bonded to the inside of the conductive members 5. In this embodiment, it is preferred that the core wire 1 be inserted after bonding; if the core wire is inserted prior to bonding, it is difficult to reach the head of the conductors 7.

Figure 7:
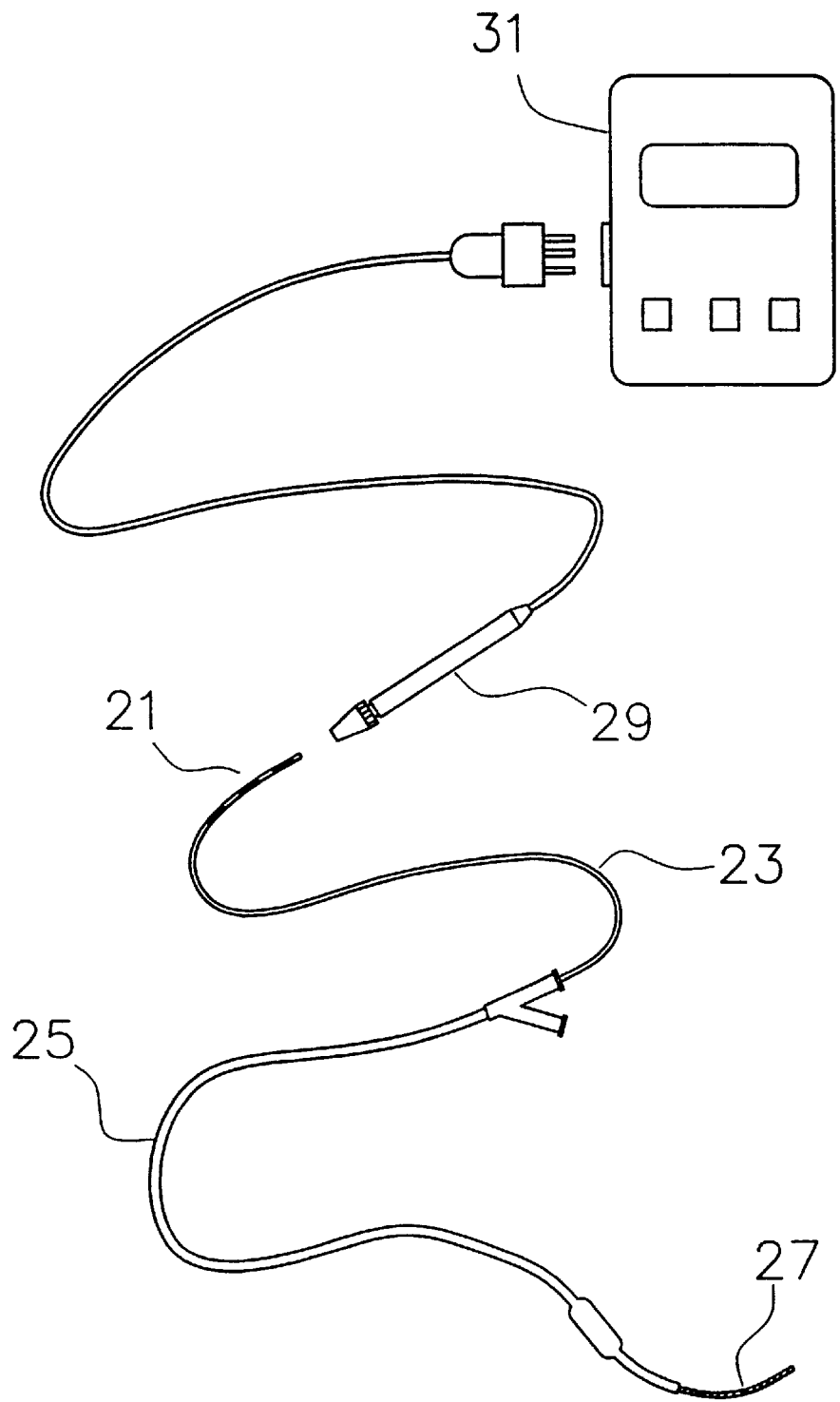
FIG. 7 illustrates a guide wire with a male connector used within a catheter, and a female connector connected to a monitor.

FIG. 7 illustrates the male cormector 21 on a guide wire 23. The guide wire 23 is inserted within a balloon catheter 25. At the distal end of the guide wire 23 is a sensor 27. The male connector 21 is inserted into a female connector 29. The female connector 29 is electrically connectable into a monitor device 31.

In practice, the distal end of the guide wire is inserted into the body, for example, into an opening into the femoral artery. Once placed by the physician into the appropriate location, a catheter 25 of the desired type is guided onto the guide wire. The guide wire is connected through the male connector 21 and the female connector 29 to a monitor 31. To permit replacement or exchange of the catheter 25, the male connector 21 is disconnected from the female connector 29, and the catheter is removed over the guide wire. At that time, body fluids would be deposited onto the connector. These body fluids would potentially create an electrical short. By providing a smooth, continuous surface, the male connector can be cleaned of these fluids. Alternatively, the female connector 29 can be provided with, for example, an O-ring at the entry point which fits snugly over the male connector, thereby cleaning the body fluids and the like from the male connector when the male connector 21 is inserted therein.

Figure 9:
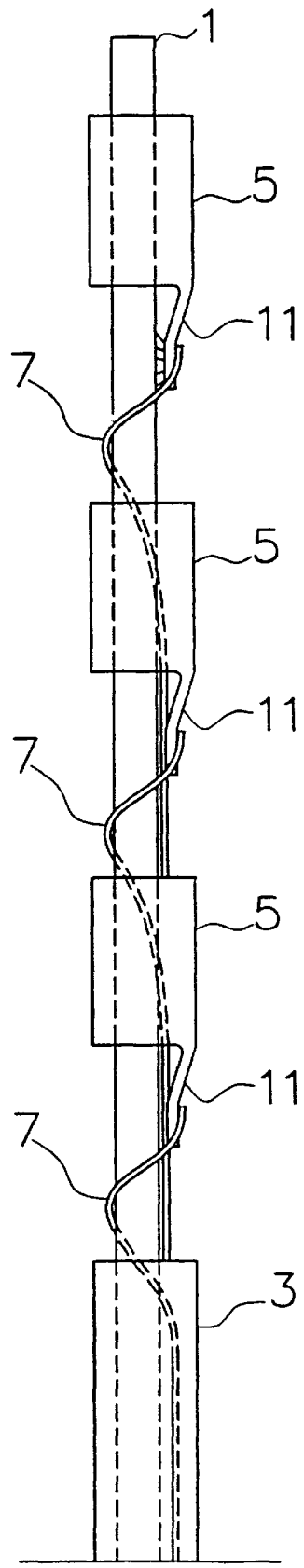
FIG. 9 illustrates an alternate embodiment of the conductors in the male connector.

FIG. 9 illustrates an alternate embodiment of the conductors 7 in the male connector. If the male connector is bent in a radius during use, a conductor near the outside of the radius will be stretched and a conductor near the inside will be compressed, with a risk that the conductors will fracture. An amount of give can be provided to the conductors 7 by not placing them parallel to the core wire, which solves this problem. For example, by winding the conductors 7 around the core wire 1, as illustrated, this problem can be solved.

Figure 10:
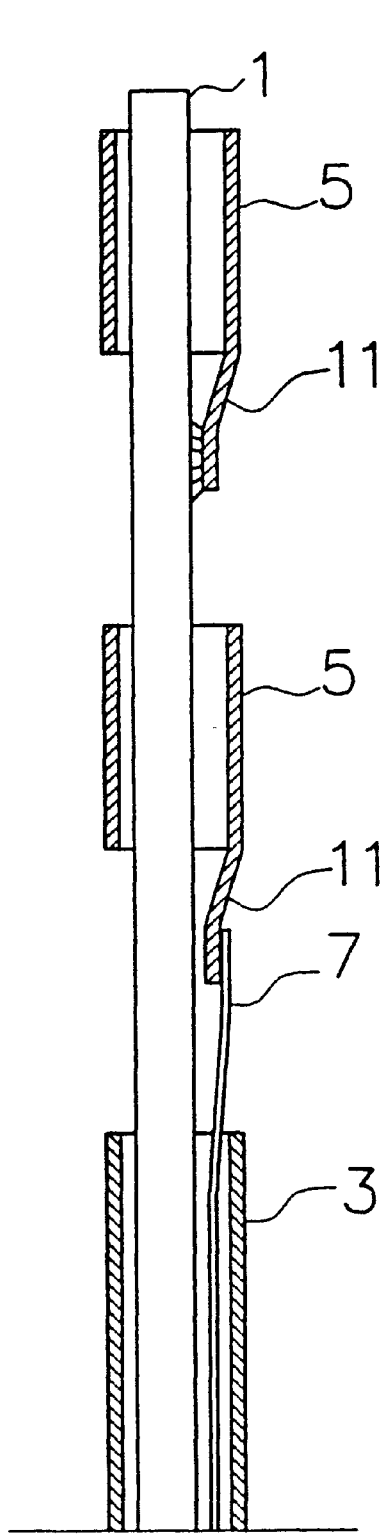
FIG. 10 illustrates a third embodiment of the male connector for a guide wire, prior to final assembly.
Figure 11:
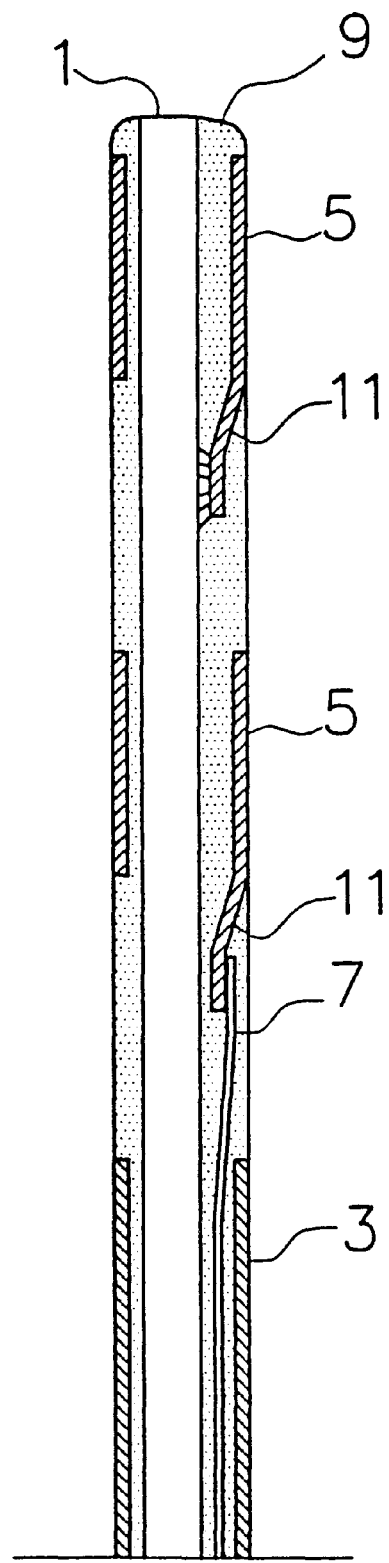
FIG. 11 illustrates the third embodiment, after final molding.

FIGS. 10 and 11 illustrate another alternative embodiment. Here, the male connector is provided with only one conductor 7 and the core wire 1 is used as the second conductor.

FIG. 12 illustrates a female connector 29 having a wiper device 32 for cleaning the male connector 21. When in use, the male connector 21 may become contaminated by bodily fluids; it is preferable to clean those fluids from the male connector before it is inserted. This can advantageously be done by equipping the female connector 29 with a wiper device 32. The wiper device 32 wipes the surface of the male connector 21 as it is inserted therein. In the illustrated embodiment, the wiper device 32 is an o-ring.

FIGS. 13–16 illustrate another embodiment of the invention. In FIGS. 13–14, the conductors 7 are embedded through the length of a plastic sleeve 34, which surrounds the core wire 1. In FIG. 13, the conductors 7 are evenly spaced radially, whereas in FIG. 14 the conductors are collected on one side of the sleeve 34 which is eccentrically-shaped. The eccentrically-shaped sleeve 34 places the core wire 1 off-center, thereby creating more space between the core wire and the outer layer for the conductors and insulation around the conductors.

Figure 15:
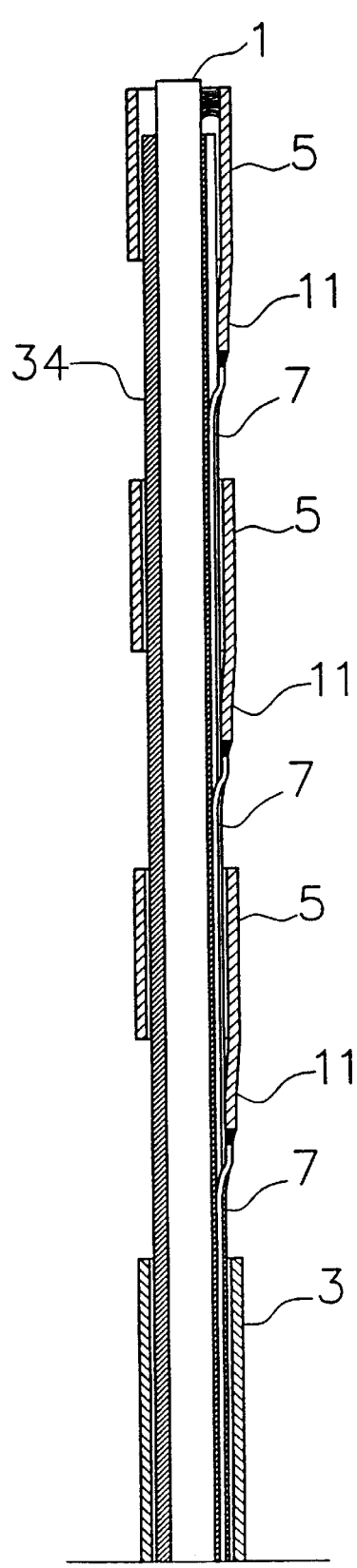
FIG. 15 illustrates one of the fourth embodiments prior to final assembly.
Figure 16:
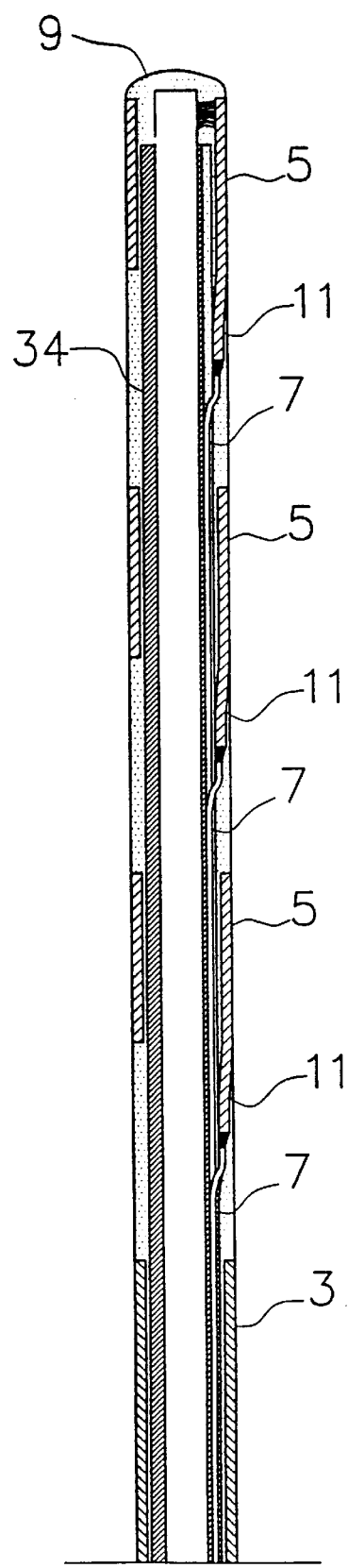
FIG. 16 illustrates one of the fourth embodiments, after final molding.

FIG. 15 illustrates the male connector of this embodiment (prior to final assembly) which comprises the conductors embedded in the plastic sleeve 34. The core wire 1 is inserted into the plastic sleeve 34. The conductors 7 embedded in the sleeve are pulled up through the sleeve 34. Conductive members 5 are connected to the conductors 7, for example by soldering or bonding. In the illustrated version, the conductive members 5 include tongues 11 to which the conductors 7 are connected. The advantage of the plastic sleeve 34 is that it prevents a potential short circuit during initial assembly. FIG. 16 illustrates the male connector of this embodiment after final assembly including insulating material 9 as described above.

Figure 17:
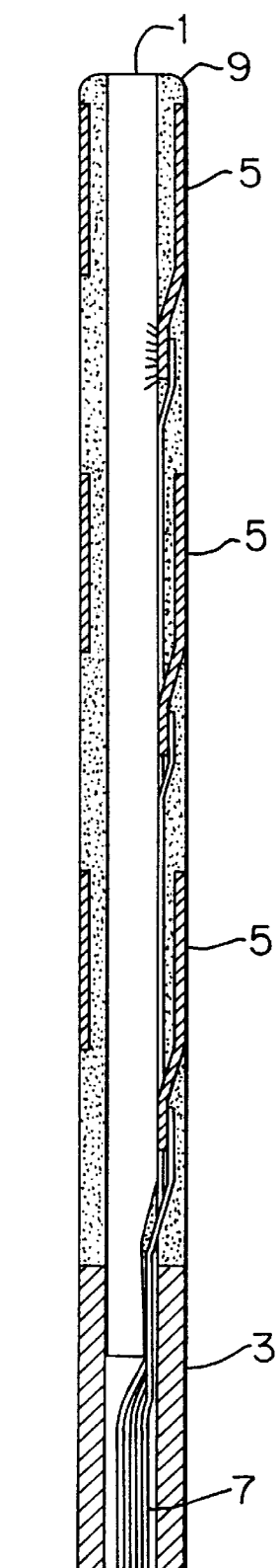
FIG. 17 illustrates a fifth alternative embodiment of the male connector for a guide wire.
Figure 18:
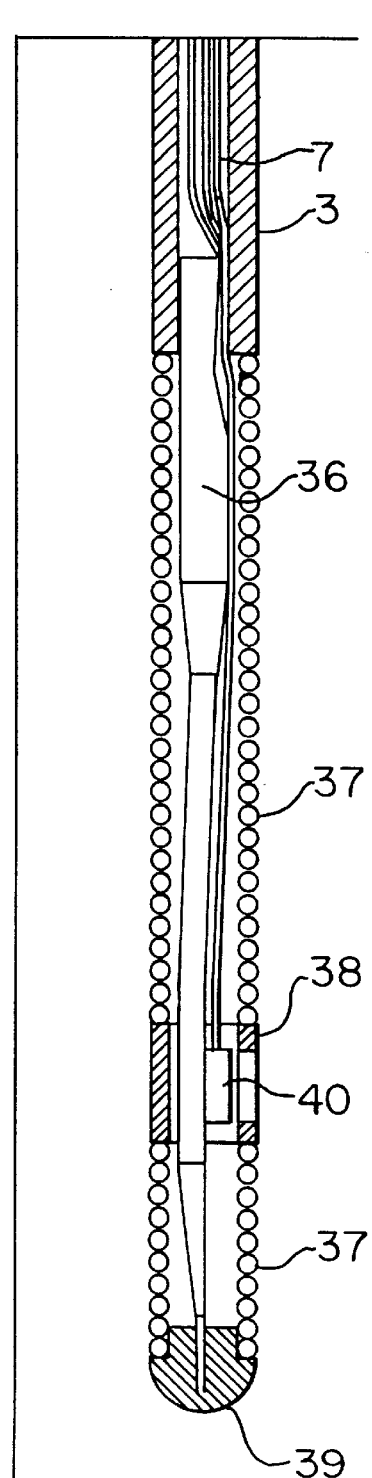
FIG. 18 illustrates a distal part of the guide wire for use in the fifth embodiment.

FIGS. 17 and 18 illustrate another embodiment of the male connector, wherein the core wire does not extend as a single piece throughout the guide wire and male connector. In order to increase a torsional strength of the guide wire with which the male connector is used, a thickness of the wall of the guide wire 3 may be increased. The practical effect is that there is insufficient space for the core wire 1 inside the guide wire.

The core wire 1 does not need to be made in one piece; as illustrated, it can be separated into parts. A first part of the core wire 1 is preferably inside the male connector, as shown in FIG. 17, where it stiffens the connector. The first part of the core wire 1 in the proximal connector is inserted a few millimeters in the proximal end of the guide wire and secured thereto such as by adhesive or solder.

The second part of the core wire 36 is inserted a few millimeters in the distal end of the guide wire and secured thereto with adhesive or solder. The portion that is inserted into the guide wire is advantageously shaped to allow passage for the conductors. The second part of the core wire 36 is preferably located inside a distal end of the guide wire, to hold a flexible distal tip coiled together.

The distal tip illustrated in FIG. 18 includes a coil 37 over a tapered core wire 36. The core wire 36 is tapered to give the desired flexibility and torsional strength of the different sections of the distal tip. The distal tip is preferably finished in a rounded tip 39, which may be of solder. A pressure sensor 40 may be connected to the conductor 7, and may be positioned near the distal tip under a protective jacket 38.

The first part of the core wire 1 and second part of the core wire 36 can be made of the same or different materials. For example, the proximal core wire 1 can be made of an insulating material, such as plastic, and the core wire 36 can be made of a high strength material, for example, stainless steel.

Figures 19, 20:
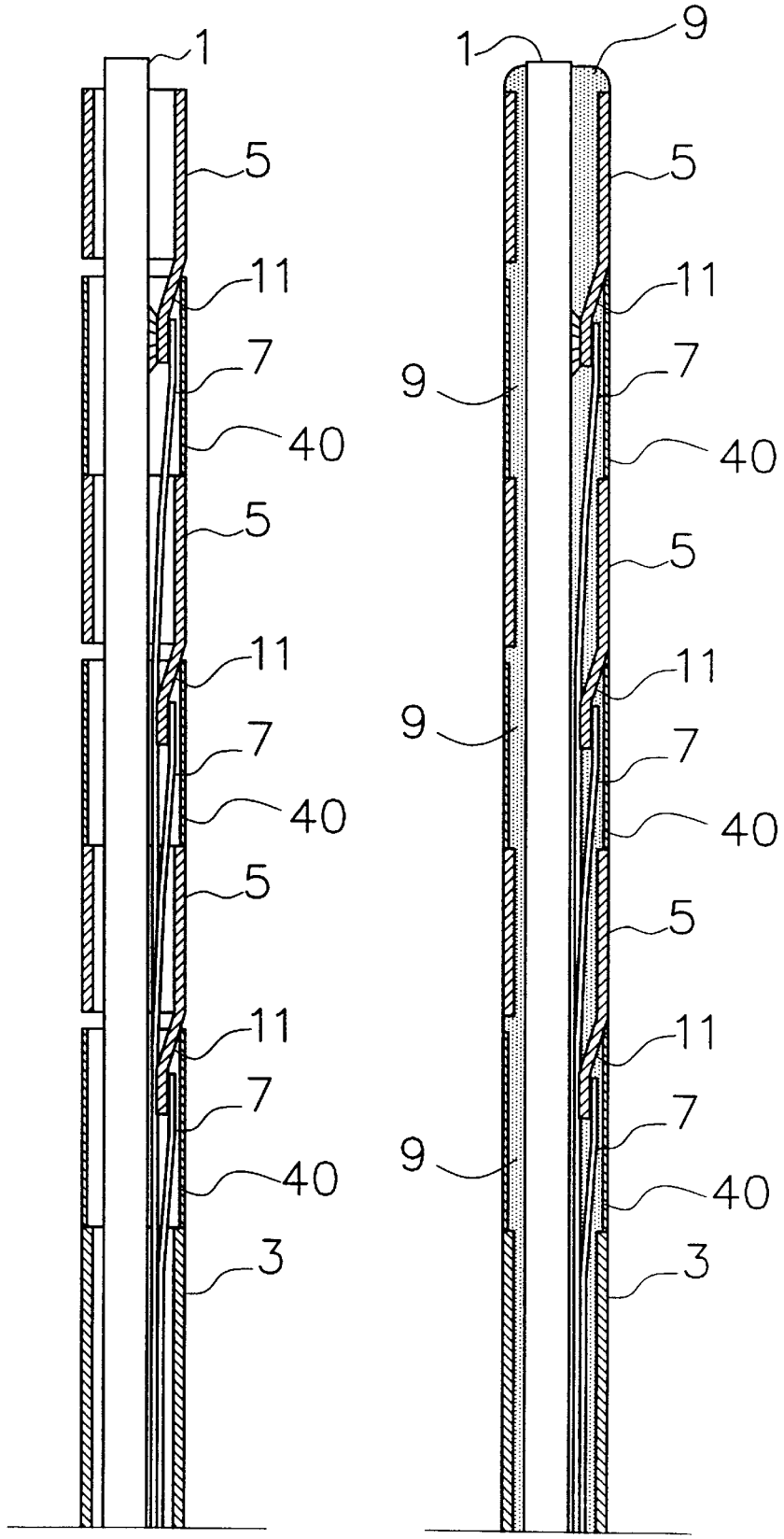
FIG. 19 illustrates a sixth alternative embodiment of the male connector for a guide wire.
FIG. 20 illustrates the sixth embodiment, after final molding.

In connection with FIGS. 19 and 20 a sixth embodiment of the invention will now be described.

The basic design is similar to the embodiment shown in FIGS. 1 and 2. An important difference is that there are provided segments 40 of polymer tubing between the conductive members 5, for providing desired spacing. The tubing segments are sufficiently thin to provide an outer shell, and such that the insulating material 9 still fills any voids inside the guide wire as a whole. Also, in order to provide for the surface of the tubing segments 40 and the surface of the conductive members 5 being coextensive, the diameter of the tubing segments should be the same as that of the conductive members. The polymer tubing 40 and the insulating material 9 will form a composite type material, which has the same function as the insulating material 9 of the first embodiment, namely to prevent capillary action from bodily fluids. In this regard, the composite is a continuous insulating material in itself. In the sixth embodiment, as in for example the first embodiment, the insulating material 9 has an outer surface coextensive with outer surfaces of the conductive members 5. The polymer selected for the tubing segments should preferably be selected to have an elasticity modulus which is higher than that of the insulating material 9. This will increase the bending resistance, i.e., make the device stiffer.

Another advantage with the provision of polymer tube segments instead of just letting the molded material provide the spacing, is that the surface of the tube segments will be smoother and more uniform, and the risk of bubbles occurring in the molded resin, and disturbing the surface smoothness is eliminated.

A further advantage is that assembly of the device is easier. In the embodiment according to FIG. 1, it may be rather difficult to locate the conductive members 5 with accuracy, in terms of the distance between them. It may be even more difficult to maintain the location during the molding procedure.

Tube segments with defined dimensions guarantee a correct distance between the conductive members 5.

Assembly is simply made by alternately threading polyimide tube segments 40 and conductive members over the core wire 1, and attaching the conductive members 5 to the conductors 7 by bonding or soldering. When the parts are assembled to the configuration shown in FIG. 19, the procedure described in relation to FIG. 1 is followed. Thus, the assembly is inserted in a flexible tube and the whole aggregate is placed in a mold (please see FIG. 4). The tube is evacuated and filled with the insulating material 9. The insulating material is cured and the aggregate is removed from the mold.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A male connector for a guide wire, the male connector comprising:
   a core wire;
   a plurality of conductive members spaced apart longitudinally along said core wire;
   an insulating material disposed between the core wire and the conductive members, the insulating material having an outer surface coextensive with outer surfaces of the conductive members; and
   at least one conductor, disposed along the core wire, connected to a conductive member.

2. A male connector as in claim 1, wherein the male connector has a diameter of about 0.355 millimeters.

3. A male connector as in claim 1, wherein the conductive members are cylindrical.

4. A male connector as in claim 2, wherein the conductive members are spaced apart from the core wire.

5. A male connector as in claim 1, the conductive member including a tongue, the at least one conductor connected to the tongue.

6. A male connector as in claim 5, wherein the tongue is bent, and the conductor is positioned on the outside of the tongue.

7. A male connector as in claim 5, wherein the tongue is straight, and the conductor is positioned on the inside of the tongue.

8. A male connector as in claim 1, wherein a proximal conductive member is connected to the core wire.

9. A male connector as in claim 1, wherein the insulating material is injection molded.

10. A male connector as in claim 1, wherein the outer surface of the insulating material and the outer surfaces of the conductive members are substantially smooth.

11. A male connector as in claim 1, further comprising an insulating coating on the core wire, between the core wire and the conductive members.

12. A male connector as in claim 1, further comprising insulating coatings on insides of the conductive members.

13. A male connector as in claim 1, wherein the at least one conductor is substantially parallel to the core wire.

14. A male connector as in claim 1, wherein the at least one conductor is wound around the core wire.

15. A male connector as in claim 1, wherein there are a plurality of conductors connected to respective conductive members.

16. A male connector as in claim 1, further comprising segments of insulating tubing between conductive members.

17. A male connector as in claim 16, wherein said segments provide desired spacing between conductive members.

18. A male connector as in claim 16, wherein the tubing is of a polymer material having an elasticity modulus higher than that of the insulating material.

19. A connector for a guide wire comprising:
   (a) a male connector as in claim 1; and
   (b) a female connector for connection to the male connector, wherein the female connector includes a wiper complementary to the male connector.

20. A method of precluding contamination by human or animal body fluid in an electrical connector having a male member and a female member, comprising:
   a) providing an elongated guide wire having a proximal end and a distal end, the male member being positioned at the proximal end thereof;
   b) forming a smooth, coextensive surface on the male member, the male member comprising a plurality of electrical conductors thereon and including insulating material and tubing segments therebetween;
   c) inserting the distal end of the guide wire into the body in the presence of body fluid;
   d) sliding a catheter over the guide wire and into the body wherein body fluids surround and enter at least a portion of the catheter;
   e) engaging the male member into the female member, the female member having complementary conductors therein;
   f) disengaging the male and female members;
   g) removing the catheter from the body by sliding the catheter over the guide wire wherein body fluids are deposited on the smooth surface of the male member; and
   h) removing the body fluids from the smooth surface without leaving body fluid on or between the conductors, thus precluding contamination.

21. A male connector as in claim 1, wherein the plurality of conductive members are located at a proximal end of the guide wire.

22. A male connector as in claim 17, wherein the tubing is of a polymer material having an elasticity modulus higher than that of the insulating material.

* * * * *